United States Patent [19]

Hirao et al.

[11] Patent Number: 5,679,824
[45] Date of Patent: Oct. 21, 1997

[54] METHOD OF PULVERIZING AROMATIC PHOSPHATES

[75] Inventors: Kiyoharu Hirao; Shouji Oda; Yukio Omoda, all of Osaka, Japan

[73] Assignee: Daihachi Chemical Industry Co., Ltd., Osaka, Japan

[21] Appl. No.: 685,532

[22] Filed: Jul. 24, 1996

[30] Foreign Application Priority Data

Sep. 22, 1995 [JP] Japan .................................. 7-244690

[51] Int. Cl.$^6$ .................................................. C07F 9/09
[52] U.S. Cl. ................................... 558/147; 558/162
[58] Field of Search ........................................ 558/147

[56] References Cited

U.S. PATENT DOCUMENTS

| 3,254,973 | 6/1966 | Giammaria . |
| 4,134,876 | 1/1979 | Horner et al. . |
| 5,122,556 | 6/1992 | Kambour . |
| 5,420,327 | 5/1995 | Bright et al. . |

FOREIGN PATENT DOCUMENTS

| 2034403 | 10/1991 | Canada . |
| 0509506 | 10/1992 | European Pat. Off. . |
| 2338284 | 7/1977 | France . |
| 51-19858 | 6/1976 | Japan . |
| 2-18336 | 4/1990 | Japan . |

OTHER PUBLICATIONS

Kosolapoff et al., "Structural Effects in Reactions of Organophosphorous Compounds. I Reactions of Phosphorous Oxychloride with Hindered Phenols", *J. Chem. Soc.*, pp. 815–818 (1968).

Kambour et al., *Journal of Polymer Science: Part B: Polymer Physics*, vol. 27, No. 10, pp. 1979–1992 and 2721 (1989).

Chemical Abstract, vol. 116, No. 12, Mar. 23, 1992, Columbus, Ohio, US, Abstract No. 107929, p. 79.

*Primary Examiner*—Johann Richter
*Assistant Examiner*—Michael G. Ambrose
*Attorney, Agent, or Firm*—Greenblum & Bernstein, P.L.C.

[57] ABSTRACT

A method of pulverizing aromatic phosphates which comprises stressing an oily product of an aromatic phosphate having a purity of 90% or more at a temperature lower by 5° to 100° C. than a melting point of the aromatic phosphate in a temperature-controllable kneader to solidify and pulverize the aromatic phosphate.

According to the present invention, aromatic phosphates industrially obtained are able to be solidified and pulverized in a short time in a simple way without being subjected to specific purification. Further, the invention is industrially advantageous in that the solidification and pulverization can be performed successively after production of the aromatic phosphate.

11 Claims, 2 Drawing Sheets

METHOD OF PULVERIZING AROMATIC PHOSPHATES

BACKGROUND OF THE INVENTION

1. Field of the Invention

The present invention relates to a method of pulverizing aromatic phosphates. More particularly, it relates to a convenient method of pulverizing an oily product of aromatic phosphate useful as flame-retardant or plasticizer for synthetic resins without subjecting it to specific purification after producing it.

2. Description of Related Art

The aromatic phosphates, used as flame-retardant or plasticizer, are able to provide resins with flame retardancy, thermal stability and/or good fabricability. Thus, they have been used as useful additives for various resins.

However, in most industrial preparation methods, the aromatic phosphates are obtained as oily products because by-products, of homologues or analogues are unavoidable. The aromatic phosphates, when added as flame-retardant or plasticizer to resins, are more advantageous in the form of powder (crystalline powder) than in the form of oil. The powdery aromatic phosphates also are more convenient for packing or transportation of product.

In order to obtain crystals from the oily product, it is required to subject the oily product to purification treatment such as recrystallization using organic solvent or fractional distillation. The purification treatment requires not only a specific apparatus or heat source but also requires collection and re-use of the organic solvent in view of preventing pollution.

Further, some of the aromatic phosphates are not easy to solidify even though they are oily products of considerably high purity, e.g., 98%.

SUMMARY OF THE INVENTION

The present inventors have felt the necessity of finding a method of solidifying and pulverizing produced aromatic phosphates without specific purification treatment and found that the oily product thereof can be solidified and pulverized conveniently and in a short time by stressing it under a condition of a specific temperature range.

Accordingly, the present invention provides a method of pulverizing aromatic phosphates which comprises stressing an oily product of an aromatic phosphate having a purity of 90% or more at a temperature lower by 5° to 100° C. than a melting point of the aromatic phosphate in a temperature-controllable kneader to solidify and pulverize the aromatic phosphate.

DESCRIPTION OF THE PREFERRED EMBODIMENTS OF THE INVENTION

Figure 1:
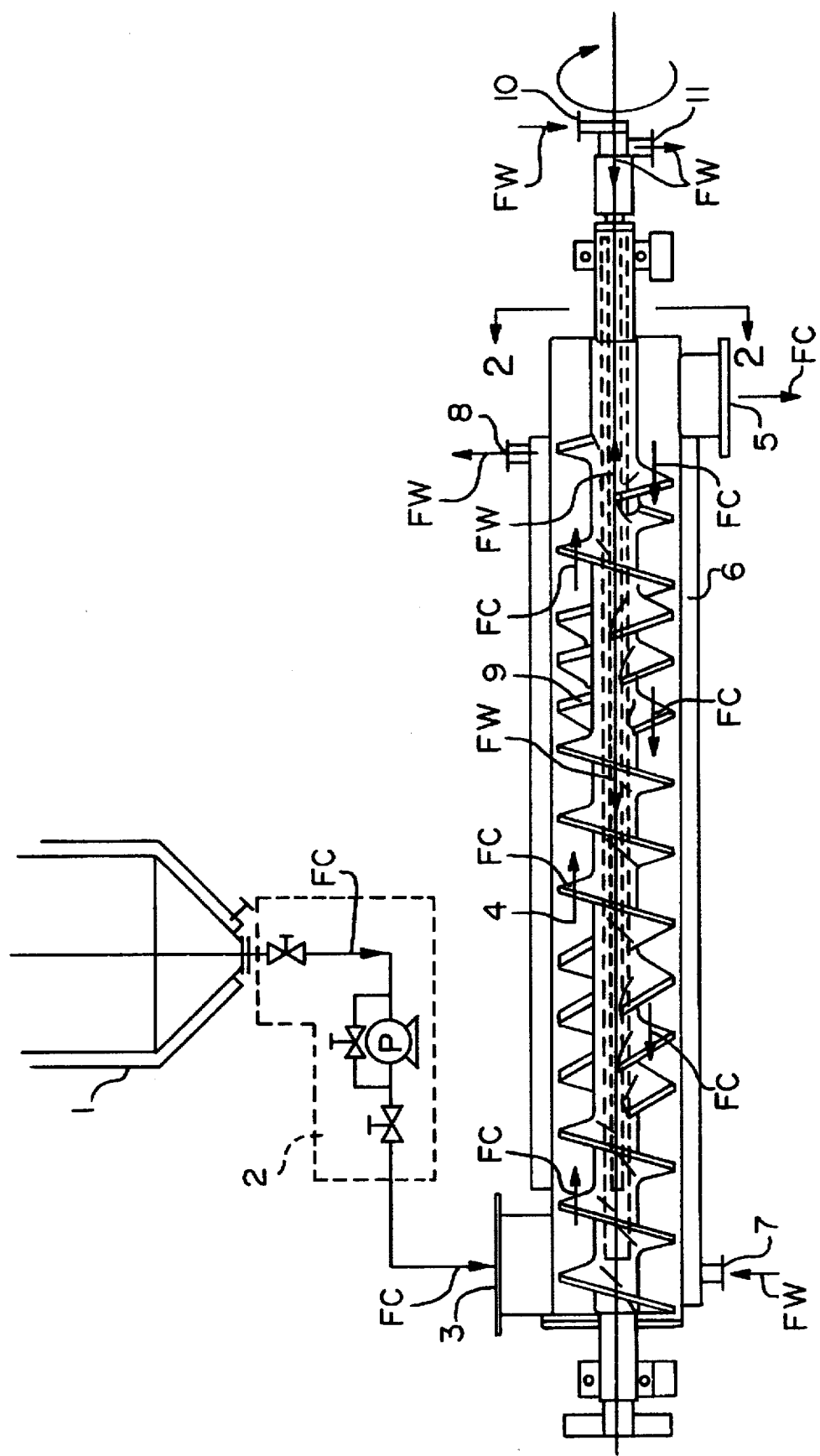
FIG. 1 is a sectional view along the rotation axis of a kneader used for the pulverization of the invention.

In the invention, it is desirable to produce the aromatic phosphate and successively use it in situ to obtain pulverized aromatic phosphate.

The oily products of aromatic phosphates usable according to the invention are the oily ones having a purity of 90% or more which are produced by industrial preparation methods, and include compounds represented by the formula (I):

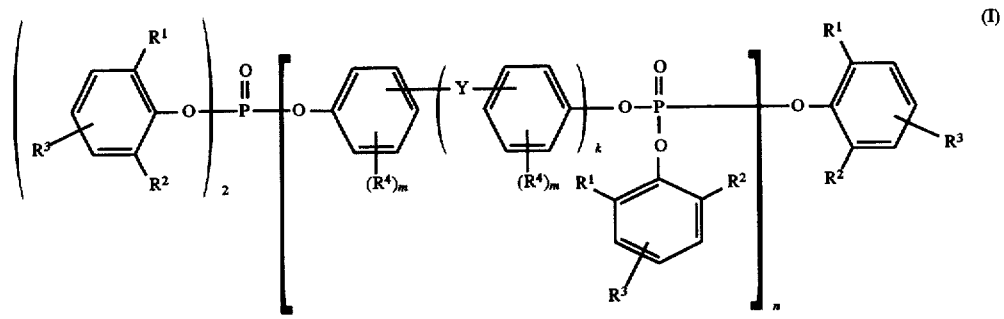

wherein $R^1$ and $R^2$ are, the same or different, a lower alkyl group; $R^3$ and $R^4$ are, the same or different, a hydrogen atom or a lower alkyl group; Y is a bond, —$CH_2$—, —$C(CH_3)_2$—, —S—, $SO_2$—, —O—, —CO—, or —N=N—; k is 0 or 1; m is an integer of 0 to 4; and n is an integer of 1 to 10.

The "lower alkyl group" in the definitions of $R^1$, $R^2$, $R^3$ and $R^4$ of the formula (I) includes a straight-chain or branched chain alkyl having 1 to 5 carbon atoms, specifically methyl, ethyl, n-propyl, iso-propyl, n-butyl, iso-butyl, sec-butyl, tert-butyl, n-pentyl, iso-pentyl, tert-pentyl and neo-pentyl, among which methyl is preferred. Preferably, $R^3$ and $R^4$ are hydrogen atoms.

Examples of the compounds of the formula (I) wherein n is 1 include aromatic diphosphates represented by the following formula:

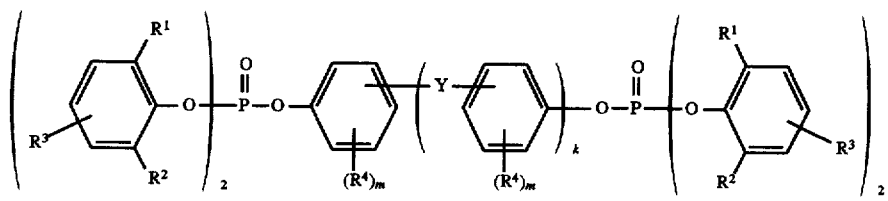

wherein $R^1$, $R^2$, $R^3$, $R^4$, Y, k and m have the same meanings as defined in the formula (I). Non-limitative preferable examples are tetrakis(2,6-dimethylphenyl)m-phenylenebisposphate [referred to as Compound (I)], tetrakis(2,6-dimethylphenyl)p-phenylenebisphosphate [referred to as Compound (II)] and tetrakis(2,6-dimethylphenyl)4,4'-diphenylenebisphosphate.

The oily product of the aromatic phosphate of the formula (I) in the invention can be synthesized, for example, by the preparation method as disclosed in European Patent Publication No. 509,506.

That is, an aromatic monohydroxy compound and phosphorus oxyhalide are allowed to react in an organic solvent in the presence of Lewis acid catalyst to obtain diarylphosphohalide and the resultant is reacted with an aromatic dihydroxy compound in the presence of Lewis acid catalyst, followed by removal of the catalysts and solvent from the reaction mixture, thereby an oily product of aromatic phosphate of the formula (I) being obtained.

The purity of the oily product thus obtained is about 90 to 98%, depending upon the raw materials, preparation method, reaction conditions and so forth. Acceptable purity for the aromatic phosphates to be used in the invention is about 90% or more, preferably about 93% or more, more preferably about 95% or more. An oily product whose purity is within the above range can be conveniently solidified and pulverized in a short time.

Any kneader conventionally used for kneading plastic materials may be utilized in the invention. The term "kneading" means, when a plastic material is mixed with several additives, giving shearing force to the material and additives simultaneously and thereby homogeneously dispersing the additives in the material. The term "stress or stressing" in the invention has the same meaning as "kneading" in the point that it means giving shearing force to the materials, i.e., stressing, simultaneously with homogenizing the temperature of the materials supplied to the kneader.

The kneaders are generally classified into batch-type such as a mixing roller, Sigma-type kneader or intensive mixer and continuous-type such as a high speed continuous feeding-type double screw mixer or extruder-type kneader. When such a kneader is adopted for solidification in the invention, it is preferable to use a continuous-type kneader which can simultaneously press the resulting solid. Also, the continuous type is advantageous in the industrial point of view because its operation capacity is high.

Especially, Ko-kneader can be suitably used in the invention, which is a kind of extruder-type kneader characteristically having strong shearing force and high ability to knead effectively and being capable of solidifying and pulverizing continuously, but the kneader in the invention is not limited thereto. A kneader which has abilities similar to the Ko-kneader can be used.

Further, the kneader may be provided with heating mechanism such as an electric resistance band heater, cast-in aluminum heater and dielectric heater, and heating or cooling mechanism such as a jacket mounted to a cylinder and a pipe mounted in a screw for running water or oil therethrough to control the temperature in the kneader.

Figure 2:
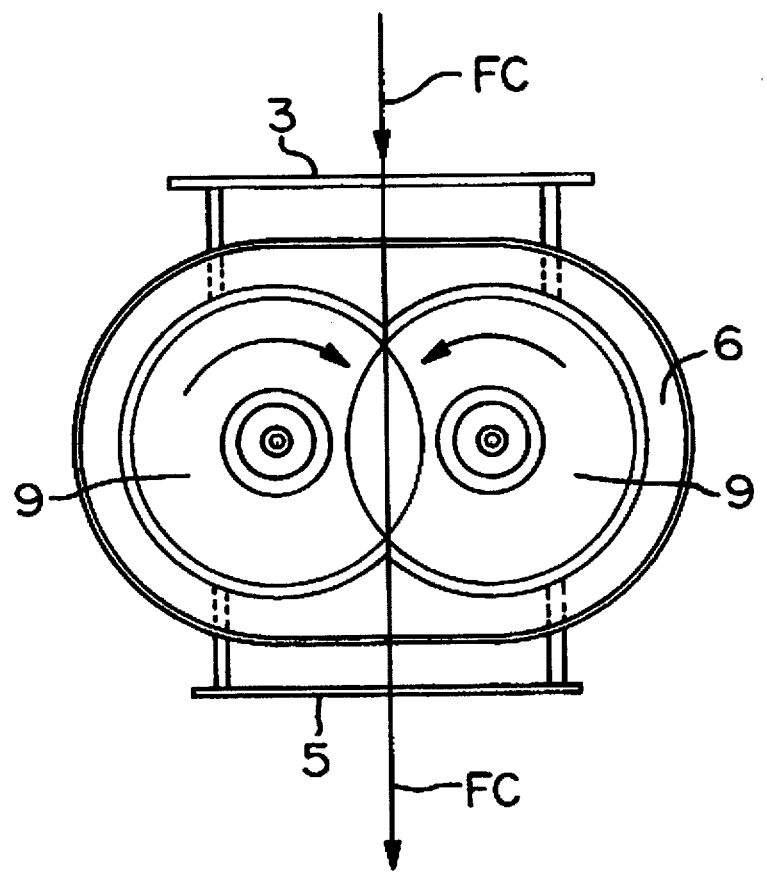
FIG. 2 is a sectional view taken along line 2—2 of FIG. 1.

Next, the process for solidification and pulverization will be explained with reference to FIGS. 1 and 2. FIG. 1 is a sectional view along the rotation axis of a kneader usable in the pulverization of the invention, and FIG. 2 is a sectional view taken along line A—A of FIG. 1. The process comprises transferring an oily product of aromatic phosphate heated at least to temperature suitable for solidification and pulverization in a tank (1) to an inlet for material (3) via a material transfer line (2) having valves and a pump, then solidifying and pulverizing the oily product continuously under stress load in a kneading part (4) including a cylinder and double screws which engage each other while they rotate reversely, and lastly discharging the aromatic phosphate powder continuously from a discharge outlet (5).

However, it is impossible to solidify and pulverize by mere kneading. It is required to control the temperature in the kneader within a suitable range. The suitable temperature range depends on thermal properties of an aromatic phosphate to be solidified; especially viscosity, fluidity and frictional heat during kneading; and also properties of an apparatus to be used. In general, the suitable temperature is lower than the melting point of the aromatic phosphate by 5° to 100° C., preferably by 10° to 70° C., more preferably by 10° to 50° C. When the temperature is within the above range, suitable stress is applied to the compound in the kneader, so that complete solidification and shortened solidification period can be achieved.

For this purpose, the kneader is provided with a jacket (6) around a cylinder for heating or cooling the oily product of aromatic phosphate as well as a screw (9) capable of heating or cooling the inside of the cylinder. For example, when the temperature is required to be lowered, a cooling fluid is passed through the jacket (6) from a fluid supply inlet (7) to a fluid discharge outlet (8) to cool the compound in the cylinder. Similarly, the cooling fluid is passed through a passage in the center of the axis of the screw (9) from a fluid supply inlet (10) provided at an end of the axis to the other end of the axis, then turned and passed through another passage formed in the outer periphery of the central passage to a fluid discharge outlet (11) provided at the end of the axis in order to cool the compound contacting the screw (9). Additionally, the arrows FC and FW in the figures show the direction of flow of the compound and the heating or cooling fluid respectively.

The oily product of aromatic phosphate to be fed into the tank (1) may be a partially solidified or liquid product of high viscosity reheated to temperature suitable for solidification. However, it is industrially more advantageous to feed an oily product of aromatic phosphate successively after producing it with at least a solvent removed to solidify it since the reheating step is not required.

Also, the oily product of aromatic phosphate to be fed may include a solvent of low boiling point in the solidification step. The low boiling solvents include lower alcohols, ethers and acetone. The low boiling solvents do not affect the properties of the aromatic phosphate since they can be easily vaporized.

Further, an additive, if necessary, may be added to the oily aromatic phosphate before the solidification.

For example, a phosphorus anti-oxidant prevents discoloration of aromatic phosphates which tend to turn yellow when heated near to the boiling point, thus improving resistance to thermal discoloration of resins when molded. The phosphorus anti-oxidants include cyclic neopentanetetraylbis(2,4-di-tert-butylphenyl)phosphite and cyclic neopentanetetraylbis(2,6-di-tert-butylphenyl) phosphite. The phosphorus anti-oxidant may be added in effective amount at any time from the production to solidification of the aromatic phosphates.

The present invention will hereinafter be explained by the following examples, without limitation thereof. In the examples, melting point was measured in accordance with JIS standard K-0064 and purity was determined by gel-permeation chromatography.

SYNTHESIS EXAMPLE 1

Tetrakis(2,6-dimethylphenyl)m-phenylenebisphosphate [Compound (I)] was synthesized by the method described in European Patent Publication No. 509,506.

In a four-necked flask equipped with a stirrer, dropping funnel, thermometer and condenser connected with water scrubber, 2,344 g (19.2 mol) of 2,6-xylenol, 192 g of xylene and 14.4 g (0.15 mol) of magnesium chloride were put and mixed with heating. When the temperature of the reaction mixture reached 120° C., 1,472 g (9.59 mol) of phosphorus oxychloride were added in about 2 hours. Generated hydrogen chloride gas was transferred to the water scrubber. After completion of the addition of phosphorus oxychloride, the reaction mixture was gradually heated to 180° C. in 2 hours in order to finish the reaction.

Then after cooling the reaction mixture to 120° C., 528 g (4.80 mol) of resorcinol and 14.4 g (0.11 mol) of aluminum chloride were added to the reaction mixture and gradually heated to 180° C. in 2 hours. The reaction mixture was stirred for 2 hours at the same temperature and then for 2 hours under a reduced pressure of 200 mmHg to complete the reaction.

Subsequently, 3,300 g of xylene and 330 g of 10% aqueous hydrochloric acid were added to the reaction mixture and stirred to remove the remaining catalyst or the like. Then the reaction mixture was washed with 990 g of 4% aqueous sodium chloride.

To the resultant mixture of the Compound (I) and the solvent [the concentration of Compound (I) being about 50 wt %], 9.92 g [0.3 wt % to Compound (I)] of 2,6-di-tert-butyl-p-cresol and then 1,320 g of 3% aqueous sodium hydroxide were added, heated to 70° C. and stirred for an hour at the same temperature.

Then, the oil phase (1320 g) of the reaction mixture was washed with 6% aqueous sodium chloride at 70° C. and further with 1,320 g of 4% aqueous oxalic acid at 90° C. to obtain 6,528 g of the oil phase [the concentration of Compound (I) being about 50 wt %]. The obtained oil phase was distilled under reduced pressure to remove xylene to obtain an oily product of Compound (I).

EXAMPLE I

In a one-liter flask having a stirrer with rotation speed indicator (HEIDON TYPE 3000H manufactured by Shinto Kagaku Kabushiki Kaisha in Japan) and a thermometer, 400 g of the oil of Compound (I) as obtained by the synthesis example 1 were put, permitted to cool with stirring at a low rotation speed and kept at 60° C. in a water bath, to which crystals of the same aromatic phosphate as Compound (I) was added as crystal seeds in an amount of 0.1 wt % to Compound (I). Then the rotation rate of the stirrer was changed to 200 rpm. From this point of time (S-point), changes in the rotation rate of a stirring blade and in the temperature in the flask due to exothermic heat were observed.

Time required for solidification is defined as a time period from the S-point to the stopping of the stirrer by rotation load. Degree of solidification is classified as follows:

Complete solidification: state of being homogeneously and completely solidified

Partial unsolidification: state of unsolidified parts remaining partially or in periphery Incomplete solidification: state of being homogeneously but incompletely solidified (though being completely solidified when the temperature lowers)

The time required for solidification was 8 minutes and complete solidification was observed.

The results are shown in Table 1 (together with those of the following Example 2 and Comparative Examples 1 and 2).

TABLE 1

| | Ex. 1 | Ex. 2 | Comparative Ex. 1 | Comparative Ex. 2 |
|---|---|---|---|---|
| Treating Temperature (°C.) | 60 | 70 | 50 | 80 |
| Time required for solidification (min.) | 8 | 8.5 | 8.5 | 25 |
| Degree of solidification | Complete | Complete | Partial | Incomplete |

The solidified substance of Example 1 was white solid having a melting point of 94° to 98° C. and purity of 96.5%, and had the following chemical structure:

EXAMPLE 2

Compound (I) was solidified in the same way as in Example 1 except that the temperature was set at 70° C. The time required for solidification was 8.5 minutes and complete solidification was observed as seen in Table 1.

COMPARATIVE EXAMPLE 1

Compound (I) was solidified in the same way as in Example 1 except that the temperature was set at 50° C. The time required for solidification was 8.5 minutes and it remained partially unsolidified as seen in Table 1.

COMPARATIVE EXAMPLE 2

Compound (I) was solidified in the same way as in Example 1 except that the temperature was set at 80° C. The time required for solidification was 25 minutes but complete solidification was not observed as seen in Table 1.

Table 1 shows that the optimal temperature range for solidifying Compound (I) is 60° to 70° C. [20° to 40° C. lower than the melting point of Compound (I)].

SYNTHESIS EXAMPLE 2

Tetrakis(2,6-dimthylpheny)p-phenylenebisphosphate [Compound (II)] as oil was synthesized in the same way as in Synthesis Example 1 except that hydroquinone was used instead of resorcinol.

EXAMPLE 3

Compound (II) was solidified in the same way as in Example 1 except that Compound (II) was used instead of Compound (I) and the temperature was set at 120°, 130°, 140° and 150° C.

The solidified substance was white powder having a melting point of 165° to 171° C. and purity of 97.0%, and had the following chemical structure:

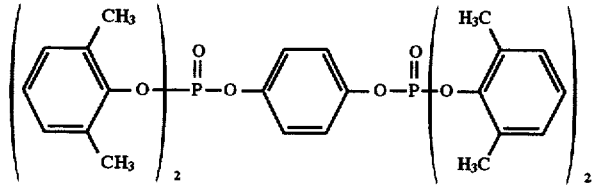

It was found that the optimal temperature range for solidifying Compound (II) was 120° to 140° C. [about 25° to 50° C. lower than the melting point of Compound (II)].

EXAMPLE 4

The oily Compound (I) as obtained by Synthesis Example 1 was solidified by using a kneader (NES-K084 type manufactured by Satake Chemical Machinery Kabushiki Kaisha in Japan, capacity: 3,000 cc) under the following conditions:

Temperature of oil when feeded: 73° C.

Feeding speed: 75 cc/min

Feeded volume: 13,500 cc

Jacket: water cooling (initial water temperature: 30° C., wasting water temperature: 35° C.)

Rotation rate for screw: 80 rpm

The product was homogeneously and completely solidified powder.

According to the present invention, since an oily product of aromatic phosphate of purity of 90% or more is forcibly pulverized by stressing at a temperature 5° to 100° C. lower than the melting point of the aromatic phosphate in a temperature-controllable kneader, aromatic phosphates industrially obtained are able to be solidified and pulverized in a short time in a simple way without being subjected to specific purification. Further, the invention is industrially advantageous in that the solidification and pulverization can be performed successively after production of the aromatic phosphate.

What is claimed is:

1. A method of pulverizing aromatic phosphates which comprises stressing an oily product of an aromatic phosphate having a purity of 90% or more at a temperature lower by 5° to 100° C. than the melting point of the aromatic phosphate in a temperature-controllable kneader to solidify and pulverize the aromatic phosphate.

2. The method according to claim 1 in which the oily product of the aromatic phosphate is supplied to the kneader successively after being produced with at least a solvent removed in order to be solidified and pulverized.

3. The method according to claim 1 in which the aromatic phosphate is represented by the formula (I):

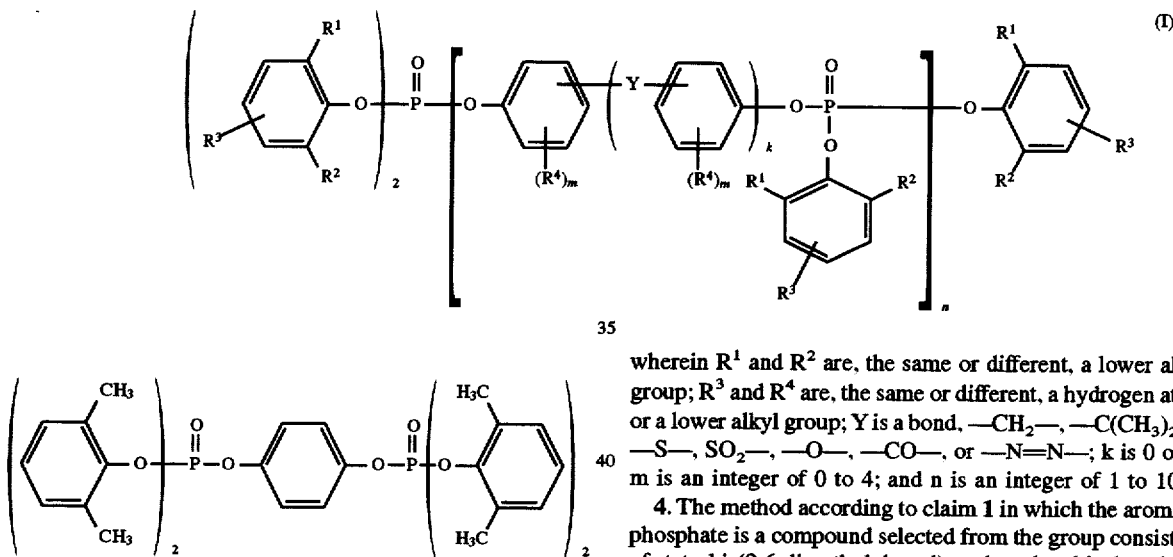

wherein $R^1$ and $R^2$ are, the same or different, a lower alkyl group; $R^3$ and $R^4$ are, the same or different, a hydrogen atom or a lower alkyl group; Y is a bond, —$CH_2$—, —$C(CH_3)_2$—, —S—, $SO_2$—, —O—, —CO—, or —N=N—; k is 0 or 1; m is an integer of 0 to 4; and n is an integer of 1 to 10.

4. The method according to claim 1 in which the aromatic phosphate is a compound selected from the group consisting of tetrakis(2,6-dimethylphenyl)m-phenylenebisphosphate, tetrakis(2,6-dimethylphenyl)-p-phenylenebisphosphate, and tetrakis(2,6-dimethylphenyl)-4,4'-diphenylenebisphosphate.

5. The method according to claim 1 in which the purity of the aromatic phosphate is about 93% or more.

6. The method according to claim 1 in which the purity of the aromatic phosphate is about 95% or more.

7. The method according to claim 1 in which the temperature of the aromatic phosphate in the kneader is 10° to 70° C. lower than the melting point of the aromatic phosphate.

8. The method according to claim 1 in which the temperature of the aromatic phosphate in the kneader is 10° to 50° C. lower than the melting point of the aromatic phosphate.

9. The method according to claim 1 in which the kneader is a continuous kneader.

10. The method according to claim 1 in which the kneader is a Ko-kneader.

11. The method according to claim 1 in which crystals of the same aromatic phosphate as the oily product are added in a small amount as seeds.

* * * * *